US007522279B1

(12) United States Patent
Liphardt et al.

(10) Patent No.: US 7,522,279 B1
(45) Date of Patent: Apr. 21, 2009

(54) SYSTEM FOR AND METHOD OF INVESTIGATING THE EXACT SAME POINT ON A SAMPLE SUBSTRATE WITH MULTIPLE WAVELENGTHS

(75) Inventors: Martin M. Liphardt, Lincoln, NE (US);
Blaine D. Johs, Lincoln, NE (US);
Craig M. Herzinger, Lincoln, NE (US);
Ping He, Lincoln, NE (US);
Christopher A. Goeden, Lincoln, NE (US); John A. Woollam, Lincoln, NE (US); James D. Welch, Omaha, NE (US)

(73) Assignee: J.A. Woollam Co., Inc, Lincoln, NE (US)

(*) Notice: Subject to any disclaimer, the term of this patent is extended or adjusted under 35 U.S.C. 154(b) by 397 days.

(21) Appl. No.: 11/447,247

(22) Filed: Jun. 5, 2006

Related U.S. Application Data

(63) Continuation-in-part of application No. 10/426,590, filed on Apr. 30, 2003, now Pat. No. 7,057,717, which is a continuation-in-part of application No. 10/050,802, filed on Jan. 15, 2002, now Pat. No. 6,859,278, and a continuation-in-part of application No. 09/583,229, filed on May 30, 2000, now Pat. No. 6,804,004.

(60) Provisional application No. 60/405,858, filed on Aug. 26, 2002.

(51) Int. Cl.
*G01J 4/00* (2006.01)
(52) U.S. Cl. ...................................... 356/364
(58) Field of Classification Search ................ 356/364, 356/445
See application file for complete search history.

(56) References Cited

U.S. PATENT DOCUMENTS

| 5,078,513 A | 1/1992 | Spaulding et al. ............. 385/14 |
| 5,091,801 A | 2/1992 | Ebstein ....................... 359/665 |
| 5,864,436 A | 1/1999 | Noyes ......................... 359/785 |
| 5,963,327 A | 10/1999 | He et al. ..................... 356/369 |
| 5,973,846 A | 10/1999 | McConica .................... 359/642 |
| 6,590,708 B2 | 7/2003 | Nakai et al. ................. 359/558 |

*Primary Examiner*—Tarifur Chowdhury
*Assistant Examiner*—Jonathon D Cook
(74) *Attorney, Agent, or Firm*—James D. Welch

(57) ABSTRACT

Disclosed are system for and method of analyzing the substantially the exact same point on a sample system with at least two wavelengths, or at least two ranges of wavelengths for which the focal lengths do not vary more than within an acceptable amount.

11 Claims, 7 Drawing Sheets

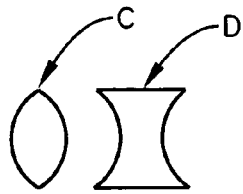
FIG. 1_f
FIG. 1_g
FIG. 1_h
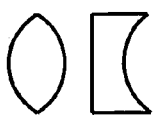
FIG. 1_i
FIG. 1_j
FIG. 1_k
FIG. 1_l
FIG. 1_m
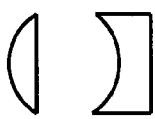
FIG. 1_n
FIG. 1_o
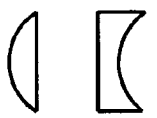
FIG. 1_p
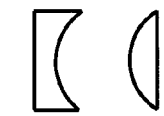
FIG. 1_q
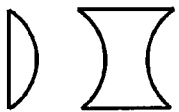
FIG. 1_r
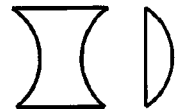
FIG. 1_s
FIG. 1_t
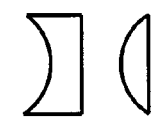
FIG. 1_u
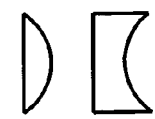
FIG. 1_v
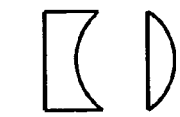
FIG. 1_w
C D C D
FIG. 1_x
C D D C
FIG. 1_y
D C D C
FIG. 1_z
D C C D
FIG. 1_zz

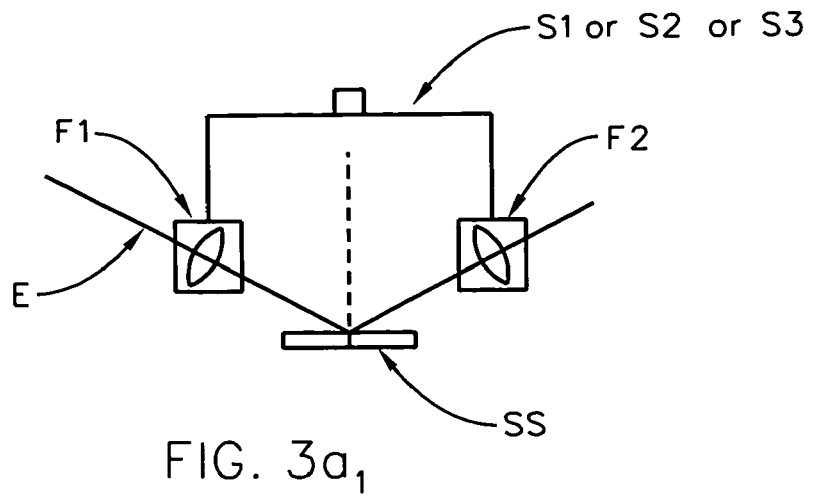
FIG. 3a₁
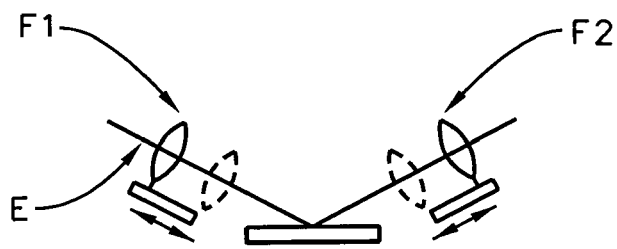
FIG. 3a₂
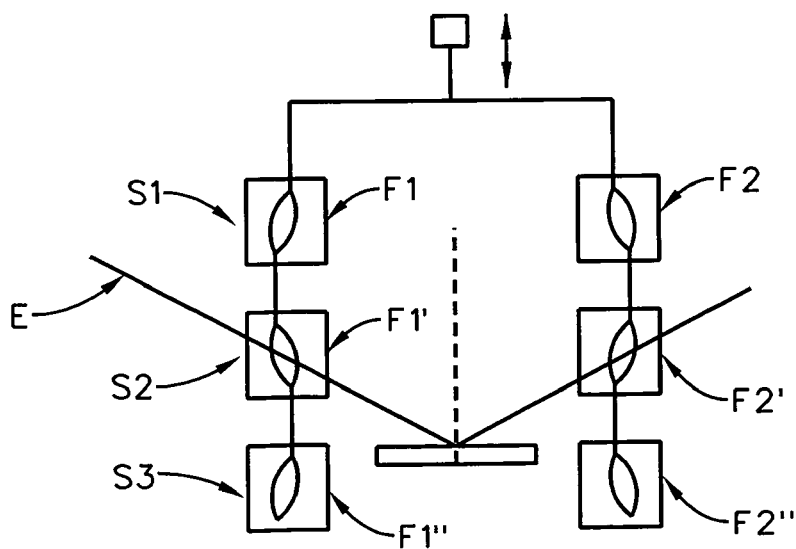
FIG. 3a₃

SYSTEM FOR AND METHOD OF INVESTIGATING THE EXACT SAME POINT ON A SAMPLE SUBSTRATE WITH MULTIPLE WAVELENGTHS

This application is a CIP of application Ser. Nos. 10/426,590 Filed Apr. 30, 2003 now U.S. Pat. No. 7,057,717, and therevia of Ser. No. 10/050,802 Filed Jan. 15, 2002 now U.S. Pat. No. 6,859,278 and Ser. No. 09/583,229 Filed May 30, 2000 now U.S. Pat. No. 6,804,004, and therevia Claims benefit of Provisional Application Ser. No. 60/405,858 Filed Aug. 26, 2002.

TECHNICAL FIELD

The disclosed invention relates to the use of electromagnetic radiation to investigate sample systems, and more particularly to a method of analyzing the exact same point on a sample system with multiple wavelengths.

BACKGROUND

It is known to investigate sample systems with electromagnetic radiation by application of ellipsometers, polarimeters, reflectometers, spectrophotometers and the like. Prior art describes the use of lenses to focus a beam of electromagnetic radiation onto a sample and to recollimate it thereafter, and known patent applications describe use of focusing and/or collimating "Achromatic" Lenses before and/or after a sample. Ideally an "Achromatic" lens provides the same focal length at all wavelengths in a beam of electromagnetism, however, practical "Achromatic" Lenses have focal lengths which vary with wavelength, in a cyclic manner about an average. That is, a plot of Focal Length vs. Wavelength rises and falls such that a line drawn substantially parallel to the Wavelength Axis passes through the plot a plurality of times. At said Focal Length then at least two, and typically more, wavelengths for which the Focal length is the same are identified. Achromatic Lenses can be designed to set two desired wavelengths, (eg. 193 nm and 248 nm), and often others will also result, on a determined, non-selected basis, at which the Focal Lengths are equal.

In ellipsometry it is often desirable to take data which pertains to multiple wavelengths, and it is also important to investigate a sample with the multiple wavelengths at exactly the same spot thereupon as well as detect resulting data for each wavelength similarly. This requires equal source and detector side focal lengths at the wavelengths.

The disclosed invention then is a system of lenses which can be focused on a sample at a plurality of wavelengths, and a method of their use in analyzing a specific spot on a sample using electromagnetic radiation applied at an oblique angle.

Another aspect of the disclosed invention is that a plurality of lens sets can be designed which provide different combinations of wavelengths at which focal lengths are equal, and the plurality of sets of lenses can be mounted in, for instance an ellipsometer system, to allow them to be sequentially positioned in the path of an electromagnetic beam, so that more wavelengths can be sequentially caused to focus on the same spot on a sample.

A primary objective of the present invention is to provide a lens or lens system which is mounted so that it can be moved toward and away from a sample, so as to sequentially cause different wavelengths to focus on the same spot on a sample at different wavelengths. Where a lens set provides equal focal lengths at each of a plurality of wavelengths, at a specific location thereof with respect to said the sample, data can be simultaneously obtained for said plurality of wavelengths.

It is also noted that supplementing a minimal number of wavelengths with increased number of angles-of-incidence can provide sufficient data sets where necessary.

A search of patents provided:
  patent to Ebstein, U.S. Pat. No. 5,091,801 which describes a nearly index matched optic formed of at least two elements for adjusting focal lengths;
  a patent to Noyes, U.S. Pat. No. 5,864,436 which describes an objective lens which has the same focal length at two wavelengths;
  a patent, U.S. Pat. No. 5,973,846 to McConica which describes an auto focus system for a digital camera which has the focus of two spectra offset from one another; and
  a patent, U.S. Pat. No. 5,078,513 to Spaulding et al., which describes a lens in a waveguide of an integrated optical waveguide which is corrected for chromatic dispersion.

Further:
  a patent to He et al., U.S. Pat. No. 5,963,327 is disclosed as the Examiner identified it in Examination of Parent application Ser. No. 10/426,590.
  a patent to Nakai al., U.S. Pat. No. 6,590,708 is disclosed as the Examiner identified it in Examination of Parent application Ser. No. 10/426,590.

Even in view of the prior art, a need remains for improved ellipsometer, polarimeter, reflectometer, spectrophotometer and the like systems which include lenses that provide the same focal length at least two wavelengths.

DISCLOSURE OF THE INVENTION

The present invention provides a method of analyzing a sample at the exact same spot with multiple wavelengths of electromagnetic radiation, and involves the steps of:

practicing steps a and b in either order, where steps a and b are:
  a) providing a selection from the group consisting of:
    ellipsometer;
    polarimeter;
    spectrophotometer; and
    reflectometer;
  which sequentially comprises a source of polychromatic electromagnetic radiation, a stage for supporting a sample and a detector;
  b) providing a lens system which has been designed to allow change of position thereof with respect to a sample, and
    optionally provide focal lengths which are substantially exactly the same at least two specified wavelengths.

The method then continues with practice of steps c-f, where the steps c-f are:
  c) placing one of the lenses provided in step b prior to a sample which is positioned on the stage for supporting a sample, and another thereof after the sample;
  d. causing polychromatic electromagnetic radiation from the source thereof to become focused onto the sample by the pre-sample lens, and obtaining data at wavelengths at which focal lengths are equal such that they are focused onto the sample at substantially exactly the same point thereupon;
  e. moving the lens systems along the locus of the electromagnetic radiation, to be at a different distance from sample and again causing polychromatic electromagnetic radiation from source thereof to become focused onto the sample by the pre-sample lens, and obtaining data at least one wavelength at which the focal length is such as to be focused onto the sample at substantially exactly the same point thereupon as in step d;

f) utilizing only data obtained which correspond to the substantially same point on the sample in sample analysis.

The disclosed method of analyzing a sample at the exact same spot can include steps a-d being repeated using a second lens system which is designed to provide the same substantially equal focal length at least two wavelengths, at least one of the at least two wavelengths being different from the two wavelengths provided by the lens systems provided in step b, and wherein step e additionally utilizes data obtained at the additional at least two wavelengths in the sample analysis.

A modified recital of the method of analyzing a sample at the exact same spot with at least two wavelengths of electromagnetic radiation, comprises practicing steps a and b in either order, the steps a and b being:

a) providing a selection from the group consisting of:
ellipsometer;
polarimeter;
spectrophotometer; and
reflectometer;

which sequentially comprises a source of polychromatic electromagnetic radiation, a stage for supporting a sample and a detector;

b) providing:

b1) a first set of two lenses which have been designed to provide focal lengths which are substantially exactly the same at two specified wavelengths; and b2) a second set of two lenses which have been designed to provide focal lengths which are substantially exactly the same at two specified wavelengths, at least one of the wavelengths being different than the two wavelengths in the first set of lenses provided in step b1.

The method then continues with practice of steps c-g, where the steps c-g are:

c) placing one of the lenses provided in step b1 prior to a sample which is positioned on the stage for supporting a sample, and one of the lenses provided in step b1 after the sample, each of the lenses being placed a focal length distance from a specific point on the sample;

d. causing polychromatic electromagnetic radiation from the source thereof to become focused onto the sample by the pre-sample lens, such that the two wavelengths are focused onto the sample at substantially exactly the same point thereupon, such that via reflection from the sample the two wavelengths are entered into the detector;

e) placing one of the lenses provided in step b2 prior to a sample which is positioned on the stage for supporting a sample, and one of the lenses provided in step b1 after the sample, each of the lenses being placed a focal length distance from a specific point on the sample;

f) causing polychromatic electromagnetic radiation from the source thereof to become focused onto the sample by the pre-sample lens, such that the two wavelengths are focused onto the sample at substantially exactly the same point thereupon, such that via reflection from the sample the two wavelengths are entered into the detector;

g) analyzing said sample utilizing only data provided by the detector based upon the wavelengths for which the focal lengths of the lenses provided in steps b1 and b2 are substantially the same.

It is also within the scope of the disclosed invention to allow the focal lengths at the two wavelengths to vary a bit, within an acceptable range. In that case the method of analyzing a sample at the exact same spot with at least two wavelengths of electromagnetic radiation, comprises the steps of:

practicing steps a and b in either order, said steps a and b being:

a) providing a selection from the group consisting of:
ellipsometer;
polarimeter;
spectrophotometer; and
reflectometer;

which sequentially comprises a source of polychromatic electromagnetic radiation, a stage for supporting a sample and a detector;

b) providing two lens systems which have been designed to provide ranges of wavelengths in Focal Length vs. Wavelength plots, for which wavelengths in the ranges of wavelengths the focal lengths are centered about two intended specified wavelengths, variance in the focal lengths being within an acceptable range.

The method then continues with practice of steps c-e, where the steps c-e are:

c) placing one of the lens systems provided in step b prior to a sample which is positioned on the stage for supporting a sample, and one of the lens systems after the sample, each of the lens systems being placed a focal length distance from a specific point on the sample;

d. causing ployochromatic electromagnetic radiation from the source thereof to become focused onto the sample by the pre-sample lens system, such that the ranges of wavelengths around the two wavelengths are focused onto the sample at substantially exactly the same point thereupon;

e) utilizing only data obtained at the wavelengths for which the focal lengths are within acceptable ranges of deviation from being substantially the same, in sample analysis.

Again, the method can involve analyzing the sample at the exact same spot in which steps a-d are repeated using additional lens systems which are designed to provide substantially the same equal focal lengths at least two additional wavelengths, using lenses which are designed to provide ranges of substantially equal focal lengths around at least two additional wavelengths, at least one of the two additional wavelengths being different from the two wavelengths provided by the lenses provided in the first practice of step b.

A modified method of analyzing a sample at the exact same spot with at least two wavelengths of electromagnetic radiation, comprises the steps of:

practicing steps a and b in either order, steps a and b being:

a) providing a selection from the group consisting of:
ellipsometer;
polarimeter;
spectrophotometer;
reflectometer; and
functional equivalent;

which sequentially comprises a source of polychromatic electromagnetic radiation, a stage for supporting a sample and a detector;

b) providing a set of two lenses which have been designed to provide a first focal length which is substantially exactly the same at first and second specified wavelengths, and a second focal length which is substantially exactly the same at third and forth specified wavelengths.

The method then continues with practice of steps c-g where the steps c-g are:

c) placing one of the lenses provided in step b prior to a sample which is positioned on the stage for supporting a sample, and one of the lenses provided in step b after the sample, each of the lenses being placed a focal length distance from a specific point on the sample;

d) causing polychromatic electromagnetic radiation from the source thereof to become focused onto the sample by the pre-sample lens, such that the first and second wavelengths are focused onto the sample at substantially exactly the same point thereupon, such that via reflection from the sample the two wavelengths are entered into the detector;

e) causing said lenses to be moved along the locus of the electromagnetic radiation toward or away from the sample, such that the said third and forth wavelengths are focused onto the sample at substantially exactly the same point thereupon as was investigated in step d, such that via reflection from the sample the two wavelengths are entered into the detector;

f) causing polychromatic electromagnetic radiation from the source thereof to become focused onto the sample by the pre-sample lens, such that the two wavelengths are focused onto the sample at substantially exactly the same point thereupon, such that via reflection from the sample said two wavelengths are entered into the detector;

g) analyzing the sample utilizing only data provided by said the detector based upon said the first, second, third and forth wavelengths.

A disclosed invention system can be described as being selected from the group consisting of:
 ellipsometer;
 polarimeter;
 spectrophotometer;
 reflectometer;
 and functionally similar systems;

which sequentially comprises a source of polychromatic electromagnetic radiation, a stage for supporting a sample and a detector. The system is characterized by lens systems which have been designed to provide focal lengths which are substantially exactly the same at two specified wavelengths, one of the lens systems being placed prior to a sample which is positioned on the stage for supporting a sample, and one of the lens systems after the sample, each of the lens systems being placed a focal length distance from a specific point on the sample.

As a specific example, the disclosed invention can also be considered to be an ellipsometer system sequentially comprising elements selected from the group consisting of:
 a. a Source of a polychromatic beam electromagnetic radiation;
 b. a Polarizer element;
 c. optionally a compensator element;
 d. focusing means;
 e. a material system;
 f. collimating means;
 g. optionally a compensator element;
 h. an Analyzer element; and
 i. a Detector System;

in which the focusing means in d and collimating means in f comprise input and output lenses mounted to allow change of position thereof with respect to a sample, and optionally provide focal lengths which are substantially exactly the same at least two specified wavelengths;

In use polychromatic electromagnetic radiation from source thereof is caused to become focused onto the sample and data is obtained at wavelengths at which focal lengths are equal such that they are focused onto the sample at substantially exactly the same point thereupon.

This is followed by moving the lenses to be at a different distances from the sample, along the locus of the electromagnetic radiation, and again causing the polychromatic electromagnetic radiation from source thereof to become focused onto the sample by the pre-sample lens, and obtaining data at least one wavelength at which the focal length is such that the polychromatic electromagnetic radiation is focused onto the sample at substantially exactly the same point thereupon as in step d; and utilizing only data obtained which correspond to the substantially same point on the sample in sample analysis.

The disclosed invention can be characterized as a lens system with application in ellipsometer and polarimeter systems wherein birefringence, and spectroscopic electromagnetic beam spot size chromatic dispersion reduction and focal length chromatic dispersion reduction is desired, wherein the lens system comprises at least two sequentially oriented elements. One of the two sequentially oriented elements is of a shape and orientation which individually converges a beam of electromagnetic radiation caused to pass therethrough, and the other is of a shape and orientation which individually diverges a beam of electromagnetic radiation caused to pass therethrough, and wherein the convergence effect is greater than the divergence effect. There is a region between the at least two elements such that, in use, a beam of electromagnetic radiation sequentially passes through one of the at least two elements, then the region therebetween, and then the other of the at least two elements before emerging as an effectively converged, focused, beam of electromagnetic radiation; the lens system being characterized in that the focal lengths at two or three wavelengths are exactly the same.

The disclosed invention can be described as a dual stage lens system with application in ellipsometer systems, where the dual stage lens system comprises two sequentially oriented lens systems, each of the two sequentially oriented lens systems being comprised of:
 at least two sequentially oriented lens elements, one of the at least two sequentially oriented lens elements being of a shape and orientation which individually converges a beam of electromagnetic radiation caused to pass therethrough, and the other being of a shape and orientation which individually diverges a beam of electromagnetic radiation caused to pass therethrough, there being a region between the at least two lens elements such that, in use, a beam of electromagnetic radiation sequentially passes through one of the at least two lens elements, then the region therebetween, and then the other of the at least two lens elements before emerging as a focused beam of electromagnetic radiation; the dual stage lens system comprising at least two sequentially oriented lens elements being a selection from the group consisting of:
  a sequential combination of a converging element, a diverging element, a converging element and a diverging element;
  a sequential combination of a converging element, a diverging element, a diverging element and a converging element;
  a sequential combination of a diverging element, a converging element, a diverging element and a converging element;
  a sequential combination of a diverging element, a converging element, a converging element and a diverging element;

the two sequentially oriented lens systems each having exactly the same focal length at two wavelengths.

In general the lense systems typically presents with a converging element selected from the group consisting of:
 a bi-convex;
 a plano-convex with an essentially flat side;
and presents with a diverging element selected from the group consisting of:
 a bi-concave lens element;
 a plano-concave with an essentially flat side.

Further, the lens systems typically comprise a selection from the group consisting of:
 a) a sequential combination of a bi-convex element and a bi-concave element;
 b) a sequential combination of a bi-concave element and a bi-convex element;
 c) a sequential combination of a bi-convex element and a piano-concave element with the concave side of the plano-concave element adjacent to the bi-convex element;
 d) a sequential combination of a bi-convex element and a plano-concave element with the essentially flat side of the plano-concave element being adjacent to the bi-convex element;
 e) a sequential combination of a plano-concave element and a bi-convex element with the essentially flat side of the plano-concave element adjacent to the bi-concave element;
 f) a sequential combination of a plano-concave element and bi-convex element with the concave side of the plano-concave element adjacent to the bi-convex element;
 g) a sequential combination of a plano-convex element and a bi-concave element with the essentially flat side of the plano-convex element adjacent to the bi-concave element;
 h) a sequential combination of a bi-concave element with a plano-convex element with the convex side of the plano-convex element adjacent to the bi-concave element;
 i) a sequential combination of a plano-concave element and a plano-convex element with the essentially flat side of the plano-concave element being adjacent to the convex side of the plano-convex element;
 j) a sequential combination of a plano-concave element and a plano-convex element with the essentially flat side of the planoconcave element being adjacent to the convex side of the plano-convex element;
 k) a sequential combination of a plano-convex element and a plano-concave element with the essentially flat side of the plano-convex element and the essentially flat side of the plano-concave element being adjacent to one another;
 l) a sequential combination of a plano-concave element and a plano-convex element with the concave side of the plano-concave element being adjacent to the convex side of the plano-convex element;
 m) a sequential combination of a plano-convex element and a bi-concave element with the convex side of the plano-convex element adjacent to said bi-concave element;
 n) a sequential combination of a bi-concave element and a plano-convex element with the essentially flat side of said plano-convex element adjacent to the bi-concave element;
 o) a sequential combination of a plano-convex element and a plano-concave element with the convex side of the plano-convex element adjacent to the concave side of the plano-concave element;
 q) a sequential combination of a plano-concave element and a plano-convex element with the essentially flat side of the plano-convex element being adjacent to the essentially flat side of the plano-concave element;
 r) a sequential combination of a plano-convex element and a plano-concave element with the convex side of the plano-convex element being adjacent to the essentially flat side of the plano-concave element;
 s) a sequential combination of a plano-concave element with a plano-convex element with the essentially flat side of the plano-convex element being adjacent to the concave side of said plano-concave element;

and wherein the region between said at least two elements has essentially the optical properties of a selection from the group consisting of:
 a void region; and
 a functional equivalent to a void region.

And further yet, each of said the at least two elements is typically made of a material independently selected from the group consisting of:
 $CaF_2$;
 $BaF_2$;
 $LiF$;
 $MgF_2$; and
 fused silica;

and wherein each of the at least two elements are individually selected to be made of different materials. One embodiment, for instance, provides lens systems wherein one of the at least two lens elements in each of the two sequentially oriented lenses is made of $CaF_2$ and the other element in each of the two sequentially oriented lenses is made of fused silica.

It is also noted that the focal length of the lens systems is often selected to be between forty and forty-one millimeters, based on practical ellipsometer system dimensions.

The invention will be better understood by reference to the Detailed Description Section of this Disclosure, in combination with the Drawings.

BRIEF DESCRIPTION OF THE DRAWINGS

FIGS. 1f-1w show various multi-element lens configurations which can provide quais-achromatic focal length vs. wavelength.

FIGS. 1x-1zz show sequences in multi-lens configurations.

FIG. 3a1 demonstrates a basic ellipsometers systems comprising lenses F1 and F2 in input and output sides of a sample system. Said F1 and F2 can be in a slidable S1, S2 or S3 as shown in FIGS. 3b and 3c, which slides into and out of the paper.

FIG. 3a2 indicates that a system can be constructed to allow moving a single lens toward or away from a sample.

FIG. 3a3 shows another approach to providing a sequence of lenses (F1) (F1') (F1") and (F2) (F2') and (F2") into the beam (E) of electromagnetic radiation.

DETAILED DESCRIPTION

Figure 1A:
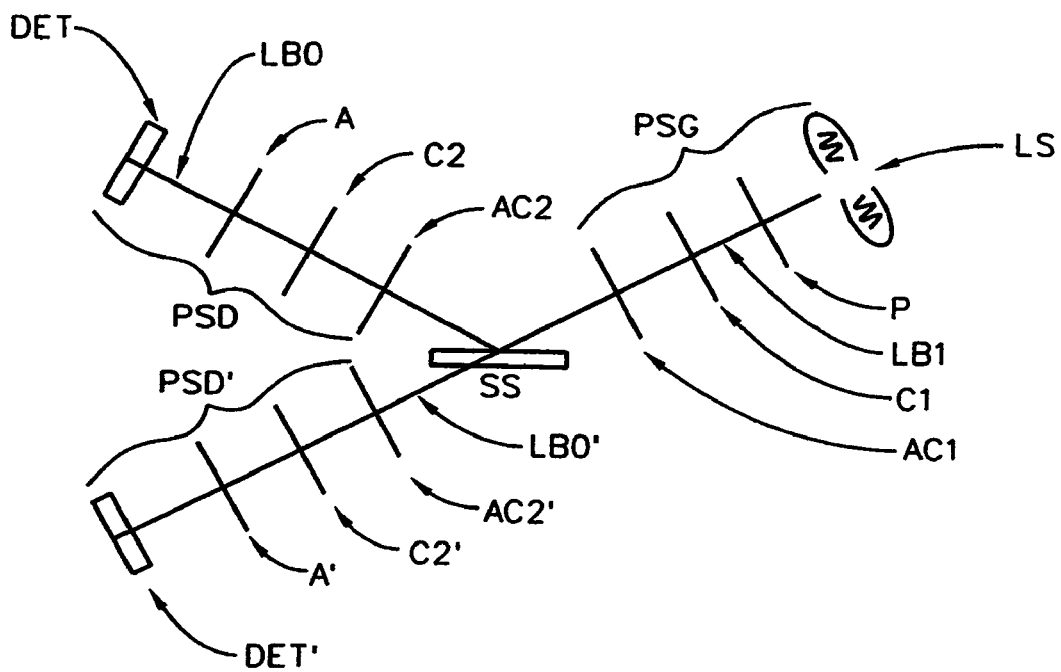
FIG. 1a demonstrates an ellipsometer system with both reflection and transmission pathways indicated.

Turning now to the Drawings, FIG. 1a demonstrates an ellipsometer or polarimeter system with both reflection and transmission pathways indicated. Note there is s Polarization State Generator (PSG) which comprises a Source of Electromagnetic Radiation (LS), a Polarizer (P), a Compensator (C1), Additional Element (AC1) which for the purposes of this disclosure can be considered to be a focusing lens, such as identified as (F1) in FIG. 1b. Also shown are Reflection and Transmission Mode Polarization State Detector Systems (PSD) (PSD') which each comprise Additional Elements (AC2) (AC2'), Compensator (C2) (C2'), Analyzer (A) (A'), and Detector (DET) (DET'). Note the Additional Component (AC2) can be considered a Focusing Lens, such as (F2) in FIG. 1b. In use the Source of Electromagnetic Radiation (LS) provides a (polychromatic) beam of electromagnetic radiation which is provided a polarizations state by Polarizer (P) and Compensator (C1), then is focused into Sample (SS) by Additional Element (AC1). After interaction with the Sample System (SS) the beam enters Polarization State Detector (PSD) (PSD'). It is note that the Compensators (C1) (C2) (C2') can be eliminated.

Figure 1B:
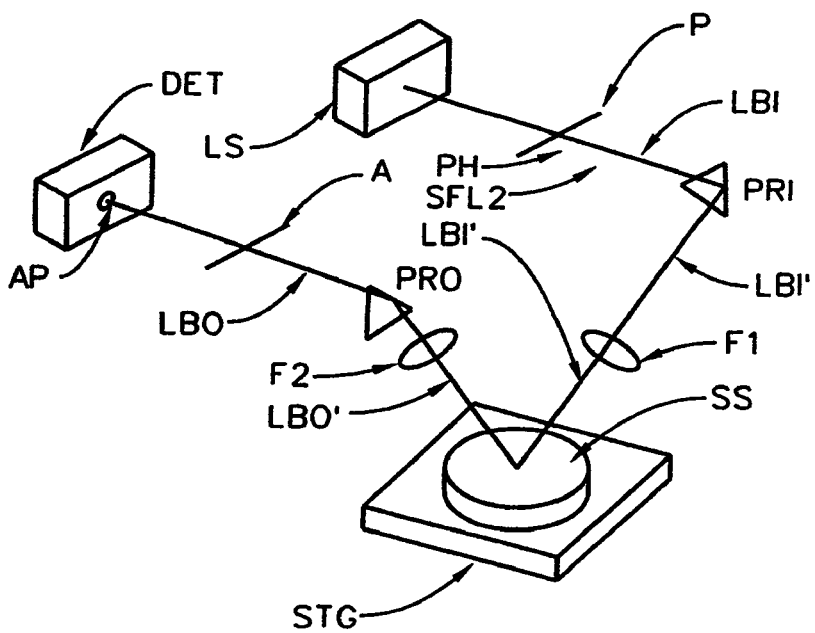
FIG. 1b shows an alternative reflection mode ellipsometer system.
Figure 1C:
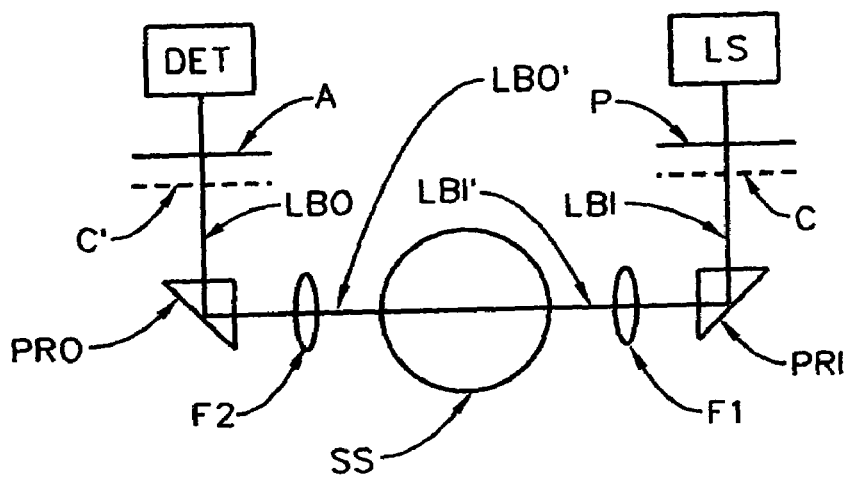
FIG. 1c shows a top view of the FIG. 1b ellipsometer system.

FIG. 1b shows a Reflection Mode variation on the System shown in FIG. 1a. Shown are a Source of Electromagnetic Radiation (LS), a Polarizer (P), a First Reflective Means (PRI), a Focusing Lens (F1), a Sample System (SS) on a Stage (STG), a Colimating Lens (F2) a Second Reflective Means (PRO), an Analyzer (A) and a Detector (DET) which provides entry thereinto via an Aperture (A). FIG. 1c shows a top view of the System of FIG. 1b. It is noted that (PRI) and (PRO) can be made of the same material, but the preferred embodiment provides that (PRI) be made of BK7 (refractive index approximately 1.55) and that (PRO) be made of F2 (refractive index approximately 1.7).

Figure 1D:
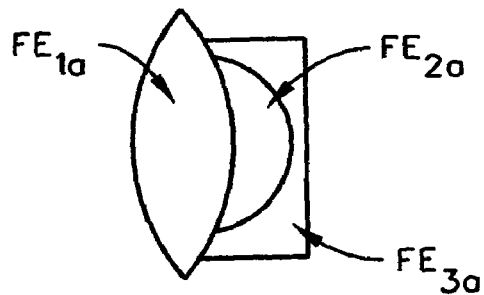
FIGS. 1d and 1e demonstrate single and multiple stage multi-element lens systems which provide quasi-achromatic focal lengths and spot sizes.
Figure 1E:
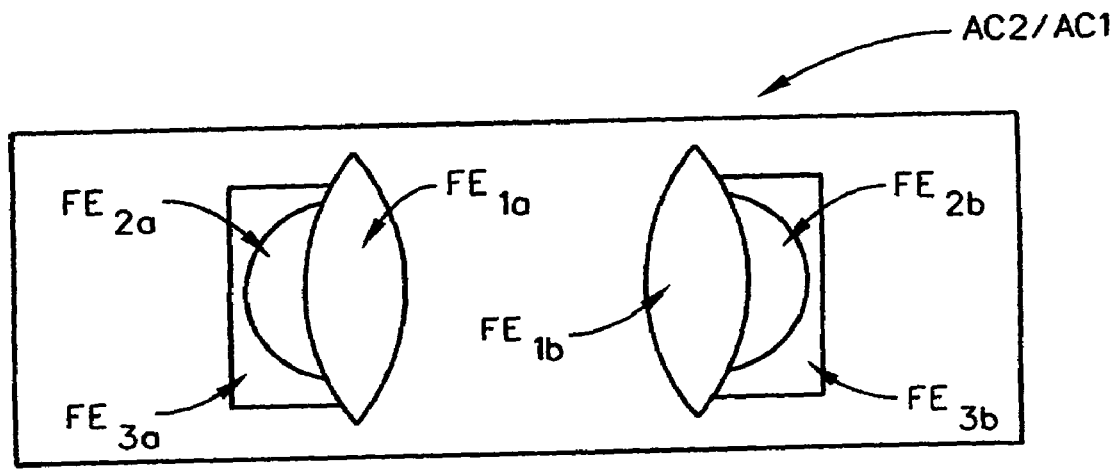

FIG. 1d shows a Lens comprised of multiple elements ($FE_{1a}$), ($FE_{2a}$) and ($FE_{3a}$). FIG. 1e shows a sequential two Lens System in which the First Lens comprises ($FE_{3a}$), ($FE_{2a}$) and ($FE_{2a}$) and in which the Second Lens comprises ($FE_{1b}$), $FE_{2b}$) and ($FE_{3b}$). The purpose of multi-element lenses is to provide more achromatic characteristics than is possible with single element lenses.

FIGS. 1f-1w are included to provide insight to various FIG. 1d Single Multi-Element Lens configurations, and FIGS. 1x-1zz are included to show that FIG. 1e two lense systems can be constructed of alternating Converging (C), (eg. the First Lens Element in FIG. 1f), and Diverging (D), (eg. the Second Element in FIG. 1f), lenses in any functional order. It is not the purpose of this Disclosure to describe any specific Lens construction, but rather to provide insight as to general Multiple Element Lens constructions, the Elements of which can be ground to provide exactly the same Focal Length at two selected wavelengths. A present invention lens system, which is particularly well suited for application in ellipsometer systems, then provides for spectroscopic electromagnetic beam spot size and focal length chromatic dispersion reduction by configuring at least two sequentially oriented elements, one of the at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between the first and second elements such that, in use, a beam of electromagnetic radiation sequentially passes through the first element, then the region therebetween, and then the second element before emerging as a focused beam of electromagnetic radiation. Such a lens system with application in ellipsometer systems is characterized by a converging element which presents as a selection from the group consisting of:
a bi-convex;
a plano-convex with an essentially flat side;

and the diverging element is characterized as a selection from the group consisting of:
a bi-concave lens element;
a plano-concave with an essentially flat side.

Further, as shown in FIGS. 1f-1w, the present invention lens systems can comprise a selection from the group consisting of:
a) a sequential combination of a bi-convex element and a bi-concave element;
b) a sequential combination of a bi-concave element and a bi-convex element;
c) a sequential combination of a bi-convex element and a plano-concave element with the concave side of the plano-concave element adjacent to the bi-convex element;
d) a sequential combination of a bi-convex element and a plano-concave element with the essentially flat side of the plano-concave element being adjacent to the bi-convex element;
e) a sequential combination of a plano-concave element and a bi-convex element with the essentially flat side of the plano-concave element adjacent to the bi-concave element;
f) a sequential combination of a plano-concave element and bi-convex element with the concave side of the plano-concave element adjacent to said the bi-convex element;
g) a sequential combination of a plano-convex element and a bi-concave element with the essentially flat side of the plano-convex element adjacent to the bi-concave element;
h) a sequential combination of a bi-concave element with a plano-convex element with the convex side of the plano-convex element adjacent to the bi-concave element;
i) a sequential combination of a plano-concave element and a plano-convex element with the essentially flat side of the plano-concave element being adjacent to the convex side of the plano-convex element;
j) a sequential combination of a plano-concave element and a plano-convex element with the essentially flat side of the planoconcave element being adjacent to the convex side of the plano-convex element;
k) a sequential combination of a plano-convex element and a plano-concave element with the essentially flat side of the plano-convex element and the essentially flat side of the plano-concave element being adjacent to one another;
l) a sequential combination of a plano-concave element and a plano-convex element with the concave side of the plano-concave element being adjacent to the convex side of the plano-convex element;
m) a sequential combination of a plano-convex element and a bi-concave element with the convex side of the plano-convex element adjacent to the bi-concave element;

n) a sequential combination of a bi-concave element and a plano-convex element with the essentially flat side of the plano-convex element adjacent to the bi-concave element;
o) a sequential combination of a plano-convex element and a plano-concave element with the convex side of the plano-convex element adjacent to the concave side of the plano-concave element;
p) a sequential combination of a plano-concave element and a plano-convex element with the essentially flat side of the plano-convex element being adjacent to the essentially flat side of the plano-concave element;
q) a sequential combination of a plano-convex element and a plano-concave element with the convex side of the plano-convex element being adjacent to the essentially flat side of the plano-concave element; and
r) a sequential combination of a plano-concave element with a plano-convex element with the essentially flat side of the plano-convex element being adjacent to the concave side of the plano-concave element;

and wherein the region between the first and second elements having essentially the optical properties of a selection from the group consisting of:
a void region; and
a functional equivalent to a void region.

A present invention lens system with application in ellipsometer systems can be further characterized in that the converging element of the first and second elements is typically made of a material independently selected from the group consisting of:
$CaF_2$;
$BaF_2$;
LiF; and
$MgF_2$;

and the diverging element of the first and second elements is selected to be made of fused silica, although it is within the scope of the present invention to make the converging element of fused silica and the diverging element of a selection from the group consisting of $CaF_2$; $BaF_2$; LiF; and $MgF_2$. It is noted that lens elements made of $MgF_2$ are typically bi-refringent whereas lens elements made of $CaF_2$; $BaF_2$ and LiF typically demonstrate far less bi-refringence, unless subjected to stress.

A present invention lens system with a focal length of fifty millimeters or less, with application in ellipsometer systems, can be described as being comprised of lens system comprising two sequentially oriented lenses, each of the sequentially oriented lenses being comprised of:
at least two sequentially oriented elements, one of the at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between the first and second elements such that, in use, a beam of electromagnetic radiation sequentially passes through the first element, then the region therebetween, and then the second element before emerging as a focused beam of electromagnetic radiation; the lens system being described by a selection, as shown in FIGS. 1x-1zz, from the group consisting of:
1. a sequential combination of a converging element (C), a diverging element (D), a converging element (C) and a diverging element (D);
2. a sequential combination of a converging element (C), a diverging (D) element, a diverging (D), element and a converging (C) element;
3. a sequential combination of a diverging element (D), a converging element (C), a diverging element (D) and a converging (C) element;
4. a sequential combination of a diverging element (D), a converging element (C), a converging element (C) and a diverging (D) element.

And, of course, other sequential lens element configurations within the scope of the present invention include:
(Converging(C))(Converging(C))(Diverging(D));
(Diverging(D))(Diverging(D))(Converging(C));
(Converging(C))(Diverging(D))(Diverging(D));
(Diverging(D))(Converging(C))(Diverging(D));
(Converging(C))(Converging(C))(Diverging (D))(Diverging(D)); and
(Diverging(D))(Diverging(D))(Converging (C))(Converging(C)).

Specific embodiments of a present invention lens system is further characterized by at least one selection from the group consisting of:
a. the focal length of the lens system is between forty (40) and forty-one (41) millimeters over a range of wavelengths of at least two-hundred (200) to seven-hundred (700) nanometers; and
b. the focal length of the dual stage lens system varies by less than five (5%) percent over a range of wavelengths of between two-hundred and five-hundred nanometers; and
c. the spot diameter at the focal length of the lens system is less than seventy-five (75) microns over a range of wavelengths of at least two-hundred (200) to seven-hundred (700) nanometers.

At least one of the input and output lenses, when selected and present, can demonstrate properties selected from the group consisting of:
both demonstrating birefringence;
neither demonstrating birefringence;
one demonstrating birefringence and the other not.

Representative materials from which different elements in the input and output lenses can be made are calcium fluoride (FE1) (FE1a) (FE1b), and fused silica (FE3), (FE3a) (FE3b).

Figure 2A:
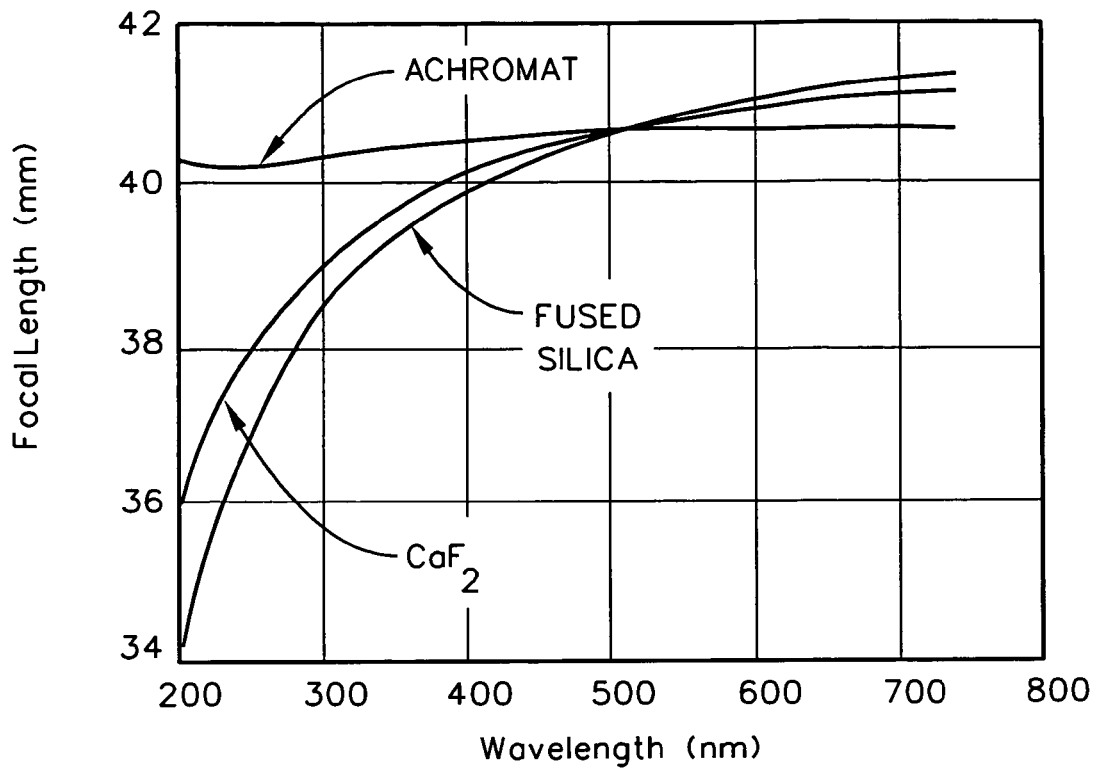
FIGS. 2a and 2b show focal length vs. wavelengths for various lens types, including quasi-achromatic lenses.
Figure 2B:
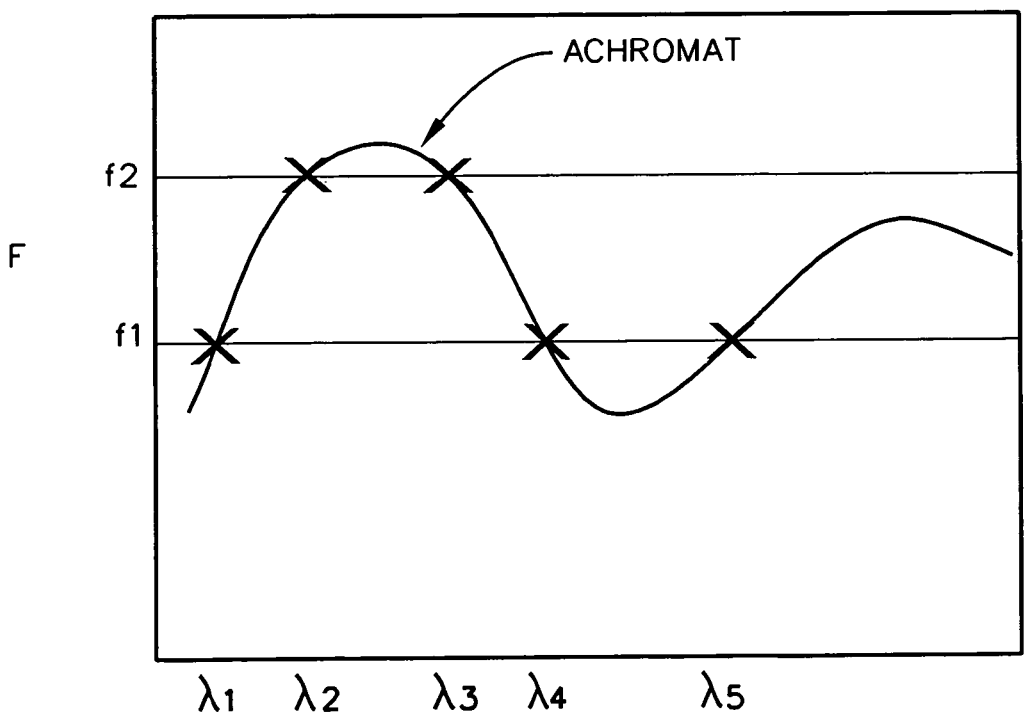
Figure 2C:
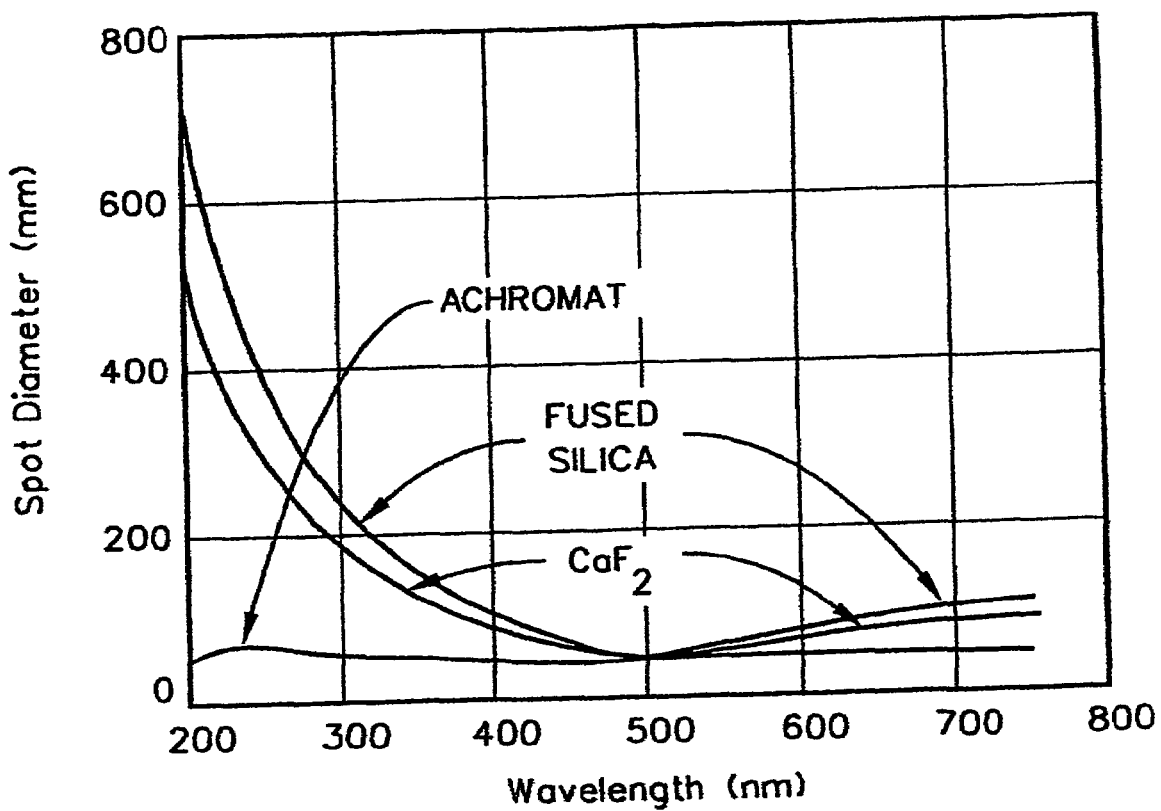
FIG. 2c shows spot size vs. wavelength for various lenses, including a quasi-achromatic lens.

FIG. 2a shows an actual Focal Length vs. Wavelength plot for a multiple element lens. FIG. 2c demonstrates Spot Size as a function of wavelength for the multiple element lens. FIG. 2b is included to show that where a cyclic variation exists in Focal Length vs. Wavelength, it is possible to identify at least two Wavelengths (2) and (3) where the Focal Lengths (f2) are exactly equal. In some cases the Focal Lengths (f1) will be exactly the same at three wavelengths (1), (4) and (5). Note that at (1) an (4) one focal length (f1) exists, and at that at (2) and (3) a second focal length exists. This gives insight that moving a single lens toward or away from a sample can cause different wavelengths to be selected at which the focal lengths are equal. Thus one embodiment of the invention allows for such lens motion as a means for enabling more than two wavelengths to investigate the same single spot on a sample. This is indicated in FIG. 3a2.

Figure 3B:
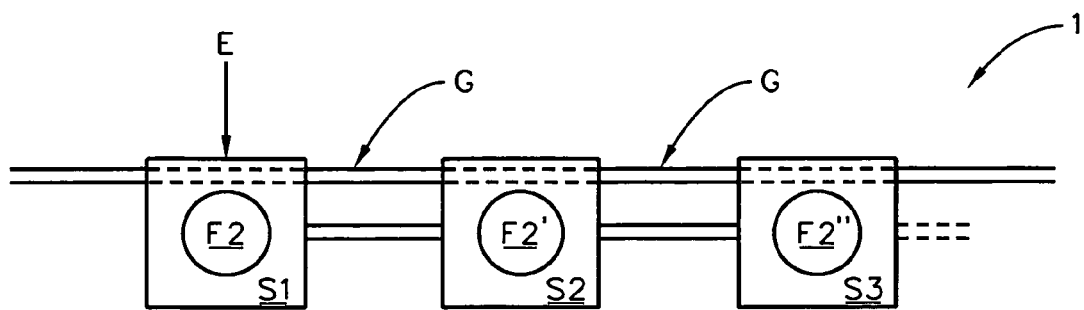
FIGS. 3b and 3c demonstrate slidable multiple input/output lens combinations.

Continuing, FIG. 3a1 demonstrates a simplified diagram showing an Electromagnetic beam (E) passing through a Converging Lens (F1), impinging on a Sample System (SS) and being recollimated by Lens (F2). FIG. 3b demonstrates that a system can be constructed to allow positioning a sequence of (S1), (S2) (S3) Systems which each contain Lens Systems (F1) (F2), (F1') (F2') and (F1") (F2"), (with F2, F2' and F2" being shown), into the pathway of the electromagnetic beam (E). A Guide (G) is shown along which the sequence of (S1), (S2) (S3) Systems can slide, which in FIG. 3a1 is into and out of the plane of the paper.

FIG. 3a2 indicates that a system can be constructed to allow moving a lens (F1) toward or away from a sample, along the locus of the electomagnetic radiation. The lens motion can be applied to adjust the focal length at a sequence of wavelengths and can enable achieving more than two wavelengths which investigate the same spot on a sample. This system allows Polychromatic electromagnetic radiation (E) from a source thereof to be focused onto the sample by the lens (F1) which is positioned before the sample, and data obtained at wavelengths at which focal lengths are equal such that they are focused onto the sample at substantially exactly the same point thereupon. Then the lenses can be positioned at a different distance from the sample, in a direction as shown, and again polychromatic electromagnetic radiation (E) from said source thereof will be focused onto the sample by the pre-sample lens (F1). Data at least one wavelength at which the focal length of the lens pre-sample lens (F1) is such as to be focused onto the sample at substantially exactly the same point thereupon as in step d can then be obtained. Only data obtained which corresponds to the substantially same point on the sample is used in sample analysis. Said data can be obtained using any number of wavelengths, as long as the correct wavelength(s) are selected at each position of the pre-sample lens (F1), with respect to the sample, so that the electromagnetic radiation is focused onto the same spot thereon. Where the pre-sample (F1) lens provides a plurality of wavelengths which have the same focal lengths at a position of the pre-sample lens (F1), with respect to the sample, then data can be simultaneously obtained thereat. However, as moving the pre-sample lens (F1) causes other wavelengths to provide focus on the same spot on the sample, the configuration of FIG. 3a2 enables obtaining data corresponding to the substantially exactly the same spot on a sample at a great many number of wavelengths. It is noted that FIG. 3a2 shows a lens (F2) after the sample, which serves to re-collimate focused electromagnetic radiation which reflects from the sample.

Figure 3C:
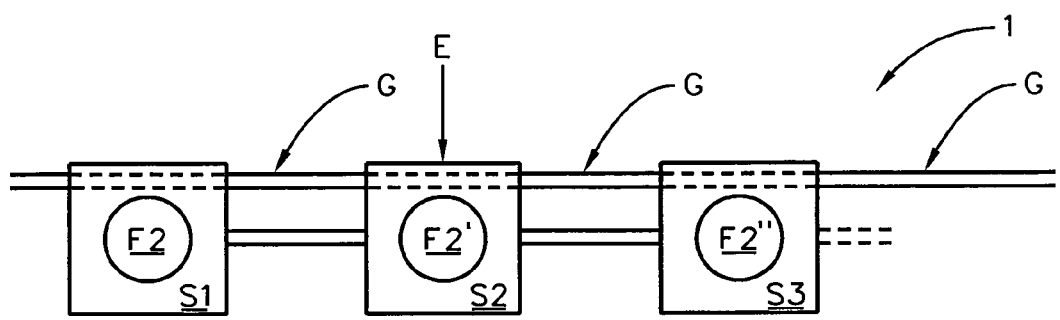

FIG. 3a3 shows another approach to providing a sequence of lenses (F1) (F1') (F1") and (F2) (F2') and (F2") into the beam (E) of electromagnetic radiation. This system allows a sequence of lenses, which are designed to provide the same focal lengths at different wavelengths, can be moved into a beam of polychromatic electromagnetic radiation (E).

It should be appreciated that by limiting data utilized to that achieved at and/or in an acceptable range around wavelengths at which the focal lengths are substantially exactly the same in analysis, it is possible to characterize a sample at a very precise point location thereupon.

Further, where two wavelengths are insufficient to adequately characterize a sample at a single spot thereupon, it is possible to provide a movable lens system, or multiple lens sets which each provide the same focal length at different wavelengths, but which wavelengths are different from set to set.

It is to be understood that the term "Point" as utilized in this Specification is to be interpreted to mean that the areas a beam of electromagnetic radiation causes on a sample by two or more wavelengths therein, are concentric about substantially the same location upon the sample.

It is also to be understood that where a system of two lenses is referred to, it is means that one lens is prior to and another after a sample. It does not mean or require that one or both of the two lenses can not each be comprised of multiple lenses, or that one or both lenses can not be of multiple element construction.

Further, where it is stated that a lens is placed at "a Focal Length" from a sample, the language is to be interpreted to include placement within practical deviations thereround.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

The invention claimed is:

1. A method of analyzing substantially the exact same spot on a sample with multiple wavelengths of electromagnetic radiation, comprising:
   practicing steps a and b in either order, said steps a and b being:
      a) providing a selection from the group consisting of:
         ellipsometer;
         polarimeter;
         spectrophotometer; and
         reflectometer;
      which sequentially comprises a source of polychromatic electromagnetic radiation, a stage for supporting a sample and a detector;
      b) providing a lens system, comprising at least one lens which len system has been designed to allow change of position of said at least one lens with respect to a sample, and which at least one lens optionally provides focal lengths which are substantially exactly the same at least two specified wavelengths;
   said method further comprising:
      c) placing said at least one lens of said lens system provided in step b prior to a sample which is positioned on said stage for supporting a sample;
      d) causing polychromatic electromagnetic radiation from said source thereof to become focused onto said sample by at least one lens positioned before said sample, and obtaining data at least one wavelength at which said electromagnetic radiation is focused onto said sample at a point thereupon;
      e) moving said at least one lens along the locus of the electromagnetic radiation to place it at a different distance from said sample and again causing said polychromatic electromagnetic radiation from said source thereof to become focused onto said sample by said lens positioned before said sample, and obtaining data at least one wavelength at which the focal length is such that the polychromatic electromagnetic radiation is focused onto said sample at substantially exactly the same point thereupon as in step d;
      f) utilizing only data obtained which correspond to said substantially same point on said sample in sample analysis.

2. A method as in claim 1, wherein said at least one lenses of the lens system comprise at least two elements and which are designed to provide focal lengths which are substantially exactly the same at two specified wavelengths.

3. A method as in claim 2, wherein each of said at least two elements is made of a material independently selected from the group consisting of:
   $CaF_2$;
   $BaF_2$;
   LiF;
   $MgF_2$; and
   fused silica;
and wherein each of at least two elements are individually selected to be made of different materials.

4. A method as in claim 1, wherein said at least one lenses of said lens system provided in step b placed prior to a sample which is positioned on said stage for supporting a sample, is characterized by a selection from the group consisting of:
  it demonstrates birefringence;
  it does not demonstrate birefringence.

5. A method of analyzing a sample at the exact same spot with at least two wavelengths of electromagnetic radiation, comprising:
  practicing steps a and b in either order, said steps a and b being:
    a) providing a selection from the group consisting of:
      ellipsometer;
      polarimeter;
      spectrophotometer; and
      reflectometer;
    which sequentially comprises a source of polychromatic electromagnetic radiation, a stage for supporting a sample and a detector;
  said method further comprising:
    b) providing a lens system, comprising at least one lense, which is designed to provide focal lengths which are substantially exactly the same at two specified wavelengths;
    c) placing said at least one lens provided in step b prior to a sample which is positioned on said stage for supporting a sample, said at least one lenses being placed a focal length distance from a specific point on said sample;
    d. causing polychromatic electromagnetic radiation from said source thereof to become focused onto said sample by said at least one lens prior to said sample, such that two wavelengths are focused onto said sample at substantially exactly the same point thereupon;
    e) utilizing only data obtained at said wavelengths for which the focal lengths are substantially the same in sample analysis.

6. A method of analyzing a sample at the exact same spot with at least two wavelengths of electromagnetic radiation as in claim 5, in which steps a-d are repeated with said at least one lenses is placed at different focal length distances along the locus of the electromagnetic radiation from said sample, so that focus is achieved at two wavelengths, at least one of which is different from the two wavelengths in step b, and wherein step e additionally utilizes data obtained at said additional different at least one wavelength in said sample analysis.

7. A method as in claim 5, wherein said at least one lenses of said lens system comprises at least two elements and which are designed to provide focal lengths which are substantially exactly the same at two specified wavelengths.

8. A method as in claim 7, wherein each of said at least two elements is made of a material independently selected from the group consisting of:
  $CaF_2$;
  $BaF_2$;
  LiF;
  $MgF_2$; and
  fused silica;
and wherein each of at least two elements are individually selected to be made of different materials.

9. A method as in claim 5, wherein said at least one lense of said lens system provided in step b placed prior to a sample which is positioned on said stage for supporting a sample is characterized by a selection from the group consisting of:
  it demonstrates birefringence;
  it does not demonstrate birefringence.

10. A method of analyzing a sample at the exact same spot with at least two wavelengths of electromagnetic radiation, comprising:
  practicing steps a and b in either order, said steps a and b being:
    a) providing a selection from the group consisting of:
      ellipsometer;
      polarimeter;
      spectrophotometer; and
      reflectometer;
    which sequentially comprises a source of polychromatic electromagnetic radiation, a stage for supporting a sample and a detector;
    b) providing at least one lenses which have has been designed to provide a first focal length which is substantially exactly the same at first and second specified wavelengths, and a second focal length which is substantially exactly the same at third and forth specified wavelengths;
  said method further comprising:
    c) placing said at least one lenses provided in step b prior to a sample which is positioned on said stage for supporting a sample, and one of said lenses provided in step b after said sample, each of, said at least one lenses being placed a focal length distance from a specific point on said sample;
    d) causing polychromatic electromagnetic radiation from said source thereof to become focused onto said sample by said lens prior to said sample, such that said first and second wavelengths are focused onto said sample at substantially exactly the same point thereupon, such that via reflection from said sample said two wavelengths are entered into said detector;
    e) causing said at least one lense to be moved toward or away from said sample along the locus of the electromagnetic radiation, such that the said third and forth wavelengths are focused onto said sample at substantially exactly the same point thereupon as was investigated in step d, such that via reflection from said sample said two wavelengths are entered into said detector;
    f) causing polychromatic electromagnetic radiation from said source thereof to become focused onto said sample by said pre-sample lens, such that said two wavelengths are focused onto said sample at substantially exactly the same point thereupon, such that via reflection from said sample said two wavelengths are entered into said detector;
    g) analyzing said sample utilizing only data provided by said detector based upon said first, second, third and forth wavelengths.

11. An ellipsometer system sequentially comprising:
  a. a Source of a polychromatic beam electromagnetic radiation;
  b. a Polarizer element;
  c. optionally a compensator element;
  d. focusing means;
  e. a material system;
  f. optional collimating means;
  g. optionally a compensator element;
  h. an Analyzer element; and
  i. a Detector System;

in which said focusing means in d comprises at least an input lense mounted to allow change of position thereof with respect to a sample, and optionally provide focal lengths which are substantially exactly the same at least two specified wavelengths;

such that in use polychromatic electromagnetic radiation from said source thereof is caused to become focused onto said sample by said at least one lens and data is obtained at wavelengths at which focal lengths are equal such that they are focused onto said sample at substantially exactly the same point thereupon;

followed by moving said at least one lense along the locus of the electromagnetic radiation to be at a different distance from said sample and again causing said polychromatic electromagnetic radiation from said source thereof to become focused onto said sample by said at least one lens, and obtaining data at least one wavelength at which the focal length is such that the polychromatic electromagnetic radiation is again focused onto said sample at substantially exactly the same point thereupon; and utilizing only data obtained which correspond to said substantially same point on said sample in sample analysis.

\* \* \* \* \*